US004001697B2

United States Statutory Invention Registration [19]

[11] Reg. Number: H1697

[45] Published: Nov. 4, 1997

Tse

[54] CONTINUOUS PROCESS FOR SODIUM METHYLATE

[75] Inventor: Shunkwok Wilson Tse, Missouri City, Tex.

[73] Assignee: E. I. du Pont de Nemours and Company, Wilmington, Del.

[21] Appl. No.: 806,808

[22] Filed: Feb. 26, 1997

Related U.S. Application Data

[60] Provisional application No. 60/013,699 Mar. 20, 1996.

[51] Int. Cl.[6] ..... C07C 31/30

[52] U.S. Cl. ..... 568/851

*Primary Examiner*—Charles T. Jordan
*Assistant Examiner*—Meena Chelliah
*Attorney, Agent, or Firm*—David E. Heiser

[57] ABSTRACT

A process is disclosed for the continuous production of sodium methylate from sodium and an excess of methanol. The process involves charging a reaction vessel with a solution of sodium methylate in methanol at a temperature of from about 80° to 86° C.; providing an inert atmosphere in the reaction vessel; agitating the contents of the reaction vessel; adding molten sodium at a metered rate to the agitated reaction vessel; adding methanol to the agitated reaction vessel at a rate which maintains the temperature of the reaction mass in a range of 80° to 86° C.; reacting the sodium and methanol for a sufficient time to substantially complete the reaction of sodium; and withdrawing from the reaction vessel a solution of sodium methylate in methanol.

6 Claims, 1 Drawing Sheet

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

CONTINUOUS PROCESS FOR SODIUM METHYLATE

This application claims the priority benefit of U.S. Provisional Application 60/013,699, filed Mar. 20, 1996.

FIELD OF THE INVENTION

This invention relates to processes for producing sodium methylate, and more particularly, to continuous processes for producing sodium methylate from methyl alcohol and sodium.

BACKGROUND

Sodium methylate is used widely as a reagent and catalyst for various chemical reactions. It is generally used as a solution in methanol for ease of handling. This may be prepared by the batch reaction of sodium metal with methyl alcohol (e.g., by adding bars, pieces, or molten sodium to a nitrogen-flushed vessel operating at atmospheric pressure and containing an excess of methyl alcohol) based on the following reaction:

$$2Na+2CH_3OH \rightarrow 2NaOCH_3+H_2.$$

This reaction is highly exothermic, and reaction heat is typically removed by boiling off and refluxing methanol. This reaction should be carefully controlled to avoid the entry of air into the reaction vessel during the feeding of the sodium, since this could mix with the hydrogen released during the reaction or with the vaporized methanol and so create an explosive mixture. The vessel is usually flushed with nitrogen or other inert gas. In large scale production, byproduct hydrogen and small amounts of nitrogen and methanol are usually vented to a flare for environmental emissions control.

The sodium charge is completed when the specified amount of sodium for the batch has been added. After the sodium has been charged, the reactor is held for a period of time until all the sodium has reacted before the product solution is transferred to a storage tank or to the point of use.

Care should be taken to avoid feeding the sodium in large portions, or at a rate faster than at which it reacts, since a large amount of unreacted sodium in the vessel at one time could cause the reaction mass to overheat and react at an uncontrollable rate. Ordinarily the reaction is vigorous and exothermic and care should also be taken to avoid feeding the sodium at a rate which generates heat faster than it can be removed (e.g., by boiling, condensing and refluxing the methanol to cool the vessel). Excess sodium feed rates can lead to an overpressure in the reactor. To avoid these hazards, slow, careful feeding of the sodium and extended reaction times have been used. During a typical batch process for the manufacture of sodium methylate, only about 50% of the reactor time or potential production capacity is actually used for the actual reaction, the remainder being spent on vessel preparation for the reaction, feeding delays and vessel shutdown steps.

German (GDR) Patent No. 118,066, discussed further below, mentions the possible continuous feeding of molten sodium to the above batch process as an alternate to feeding solid sodium portions, but dismisses the possibility because it was believed a large expense for safety equipment for the feeding device would be required.

Numerous efforts have been made to develop alternate processes in which hazards are minimized. For example, many patents such as U.S. Pat. No. 4,596,895 disclose the reaction of sodium amalgam with methanol as a means to produce sodium methylate. Such processes require the use of various catalysts to promote the reaction, use of highly toxic mercury, and a convenient source of the sodium amalgam (previously available from amalgam-based caustic/chlorine plants). German Patent No. 118,066 discloses a process for the continuous manufacture of sodium methylate by continuously and separately adding methanol and a sodium dispersion in an alcohol-immiscible, inert organic solvent to a reactor, mixing and reacting at 20° to 75° C. using high frequency agitation, and removing the methanol-solvent mixture containing the sodium methylate. This process requires the use of an inert organic solvent, the preparation of a dilute sodium dispersion in this solvent, and the removal of this solvent from the sodium methylate solution.

There is a need for a continuous process for the manufacture of sodium methylate from sodium and methanol which does not require the use of an extra ingredient and added preparation and purification steps, and which avoids the inefficient use of reactor capacity and safety problems associated with intermittent feeding of sodium during the batch process.

SUMMARY OF THE INVENTION

A process is provided in accordance with this invention for the continuous production of sodium methylate from sodium and an excess of methanol. The process is characterized by charging a reaction vessel with a solution of sodium methylate in methanol at a temperature of from about 80° to 86° C.; providing an inert atmosphere in the reaction vessel; agitating the contents of the reaction vessel; adding molten sodium at a metered rate to the agitated reaction vessel; adding methanol to the agitated reaction vessel at a rate which maintains the temperature of the reaction mass in a range of 80° to 86° C.; reacting the sodium and methanol for a sufficient time to substantially complete the reaction of sodium; and withdrawing from the reaction vessel a solution of sodium methylate in methanol.

DETAILED DESCRIPTION

Figure 2:
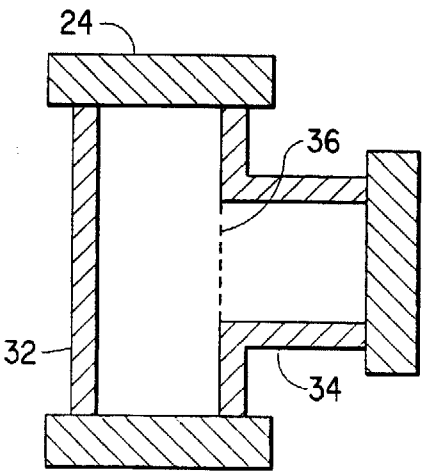
FIG. 2 is a cross-section drawing of a suitable screen filter used in the production unit of FIG. 1.

In the process of this invention sodium is fed into a reactor at a fixed or metered rate, and methanol is fed into the reactor at a variable or controlled rate, based on reaction temperature. The desired temperature may be maintained by increasing the flow of methanol if the temperature exceeds a desired setpoint and decreasing the flow of methanol if the temperature drops below the desired setpoint. The reactor temperature correlates to the sodium methylate concentration which is an important quality parameter for the finished product. The flow of methanol is increased if the reactor temperature exceeds the desired set point because a high temperature indicates is that the reactor solution has too high a boiling point and is therefore too concentrated. Too low a reactor temperature indicates too low a boiling point and too low a concentration, so the flow of methanol is decreased. In this manner, the desired concentration of sodium methylate in methanol is achieved by the selection of the temperature setpoint and thus the boiling point of the sodium methanol solution.

The pressure in the reactor is generally a key measurement of the amount of reactive sodium in the reactor and is a function of the sodium feed rate. High reactor pressure indicates sodium buildup in the reactor or a restriction in the vent system, and reactor pressure can be interlocked with sodium feed so as to shut off the sodium feed at excessive pressure.

Sodium may be received in a tank car as a solid, and melted in the tank car by circulating heated oil through the jacketed coil in the tank car. The tank car may then be used as a storage tank for containing the molten sodium. Alternatively, a separate storage tank with a weigh cell may be used. The molten sodium is typically transferred to the reaction vessel by means of a heated pipeline. Preferably, the sodium is fed to the reactor at a metered rate, chosen according to production demand but not to exceed the maximum demonstrated reaction rate for the apparatus used. By feeding "at a metered rate" is meant that the flow is predetermined and essentially constant, and varied only by discrete steps, rather than being continually adjusted and varied. The maximum reaction rate for a particular system is a function of the size of the reactor, the intensity of agitation in the reactor, the cooling capacity of any methanol reflux system, and the capacity of any vent and flare system, among other factors. For metering the flow rate of the molten sodium, a mass flow meter manufactured by Micromotion Co., has been found to be satisfactory.

A solution of sodium methylate in methanol is withdrawn from the reaction vessel. Withdrawal of the sodium methylate solution is preferably continuous. Sodium methylate product can be continuously transferred from the reactor to a storage tank by controlling the reactor to maintain constant level. While the reaction is normally continued for a sufficient time to substantially complete the reaction of sodium, the portion of the reaction mass removed from the reaction vessel may contain unreacted sodium. Unreacted sodium in the solution may be screened off in the transfer stream or kept inside the reactor by an internal screen.

The reaction vessel is charged with a solution of sodium methylate in methanol. It is preferred to make a fresh batch of sodium methylate by a batch operation to fill the reactor to operating level and then switch to a continuous mode of operation. For example, the reaction vessel may be filled about 60% full with a solution of sodium methylate in methanol at about the desired strength and at a temperature of 80° to 86° C. before starting the reaction in continuous mode.

When running continuously, the reactor temperature controller controls the methanol flow to maintain the reactor temperature at its chosen set point. This temperature set point determines the strength of the sodium methylate solution produced since the normal boiling point of the solution varies with concentration, and since the reactor will be operating at or near its boiling point. The ratio of methanol flow to sodium flow will normally range from about 8:1 to 10:1 by weight depending on the desired strength of the sodium methylate solution.

Preferably the sodium methylate strength is about 28% by weight, or less (the reaction slows down when the reaction mass has too high a strength, and sodium could then build up). The accidental overfeeding of a large methanol flow (e.g., because of the sodium buildup problem) could lead to overpressuring the reactor and possible escape of raw materials. This could create hazardous conditions because sodium can react vigorously with moisture and lead to a fire (the reactor vapor of hydrogen and methanol can form an explosive cloud) and because exposure to sodium methylate can itself be harmful to the human body. Accordingly, a reaction pressure relief system may be employed. To mitigate the possibility of overpressuring the reactor due to overfeeding a large methanol flow, an orifice can be placed in the methanol feed line to limit its feed rate to within the design capacity of the reactor pressure relief system.

As an added safety feature, the reaction system can also contain a high temperature process interlock designed to shut off sodium feed at 88° C., the boiling point of 30% sodium methylate solution.

As another safety procedure (i.e., a check against an unexpected mount of excess sodium in the reactor) the sodium and methanol feeds can be shut off periodically (e.g., every 2 hours) for an interval (e.g., 4 minutes) sufficient to check the rate of reactor pressure decrease. If the reactor pressure drops to an acceptable level during the interval (e.g., to 12 inches (30 cm) of water in 4 minutes), the sodium and methanol feed will resume. If not, the process feeds will be shut off by an interlock. Usually, reactor pressure is a dependable measure of the amount of reactive sodium in the reactor.

The relationship of the sodium methylate solution strength and its normal boiling point is shown in Table 1 below. An automatic calculator can be used to determine the temperature control from the desired sodium methylate solution set point, or this may be calculated manually by the relationships later shown. The reactor normally operates at temperatures between 80° and 86° C. depending on the desired solution strength. The temperature control system is preferably designed so that a temperature higher than the desired set point increases the flow of methanol into the system; and a temperature below the desired set point reduces methanol flow.

TABLE I

| Boiling Point degrees Celsius | Sodium Methylate Concentration in weight % |
|---|---|
| 80 | 22 |
| 81 | 23 |
| 82 | 24 |
| 83 | 25 |
| 84 | 26 |
| 85 | 27 |
| 86 | 28 |

In a preferred commercial embodiment, the reactor operates at essentially atmospheric pressure and vents to brine-cooled condensers and to a flare. If desired, the brine coolers may be preceded by air coolers to reduce the cost of refrigeration. By essentially atmospheric pressure is typically meant a pressure of only about 10 to 18 inches (25 to 45 cm) of water pressure. This pressure is determined by the back pressure of flows through the condenser and vent system to the atmosphere and may be somewhat higher or lower in other reaction units depending on equipment size.

The product, a solution of sodium methylate in methanol, can be removed from the reaction vessel to a storage tank at a rate set by a level control device, so as to provide a constant reaction volume and reaction hold time. Preferably, the reaction mass is withdrawn from near the bottom of the reaction vessel and recirculated back to the top of the vessel so as to help maintain a uniform concentration of any particulate sodium throughout all levels of the reaction mass. Preferred embodiments of the process include embodiments using a recirculation loop wherein a portion of the reaction mass is removed from the reaction vessel and transferred to a filter or screen which separates a filtered portion of the reaction mass for use as product solution and returns the remainder back to the reaction vessel, and embodiments using a filter or screen placed inside the reaction vessel, wherein the product is withdrawn through the filter or screen. For example, the product solution of sodium methylate in methanol may be withdrawn as a side stream from such a recirculation line or loop through a self-cleaning filter which prevents any significant amount of particulate sodium from leaving the reaction system and entering the product storage tank where it would continue to react.

Figure 1:
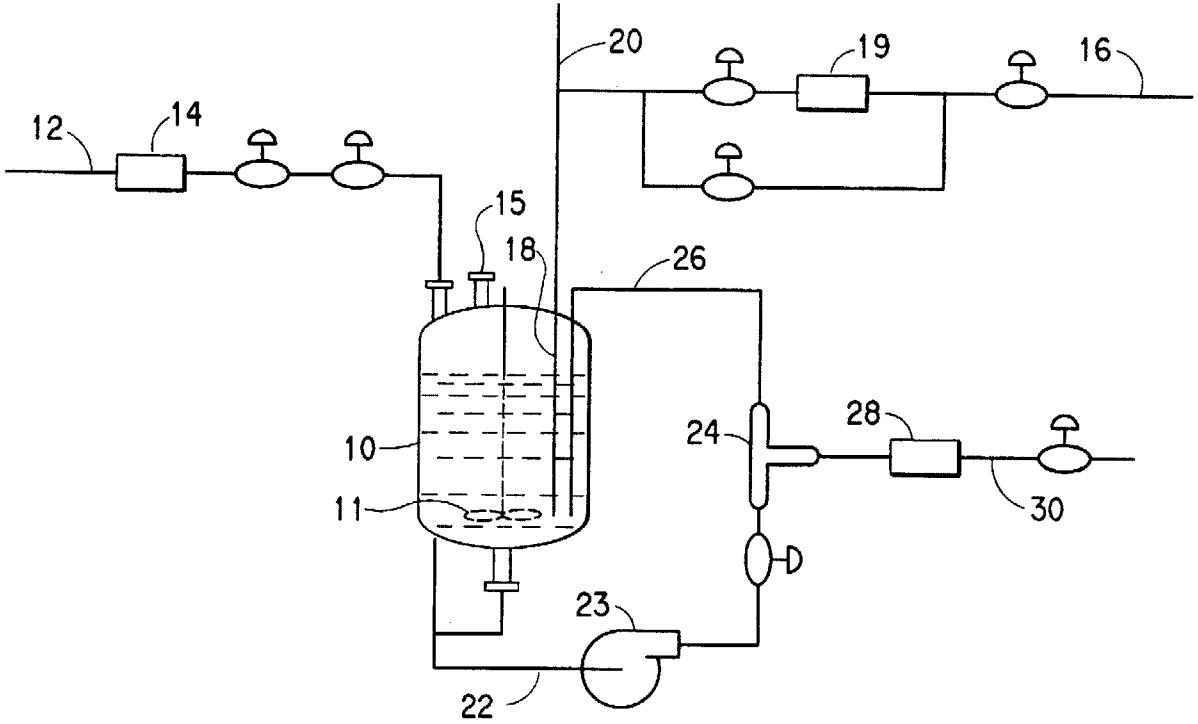
FIG. 1 is a schematic drawing of a typical production unit utilizing this invention.

A production unit employing the process described herein is schematically illustrated in FIG. 1. The agitated reaction vessel 10 containing agitator 11 has suitable inlets for sodium, methanol and nitrogen and outlets for product and vapors. Vapor outlet 15 is near the top of the vessel 10. Molten sodium from a storage unit (not shown) is transported through line 12 to the reactor 10, though a mass flow meter 14, provided to control flow rate. Methanol is transported through line 16 to a dip-leg 18 in the reaction vessel. Flow is controlled by controller 19 based upon reactor temperature as previously described. A line 20 is provided for the return flow of methanol from the reflux/cooling system, and joins line 16, the combined flow of methanol entering the vessel through dip-leg 18. Reaction mass is withdrawn from at or near the bottom of the reaction vessel through line 22 and is pumped by pump 23 to a screen filter 24. The portion of the withdrawn reaction mass containing unreacted sodium particles which may be present in the mass withdrawn from the reaction vessel is recycled back to the reaction vessel via line 26, and the filtered product portion of the withdrawn reaction mass, leaves the system through a level control device 28 via line 30. A suitable design for the self-cleaning filter 24 is shown in FIG. 2. It includes a ranged section of pipe 32 mounted vertically with a side outlet 34 which contains a filter screen 36 to prevent sodium particles from leaving the reactor system. The filter screen 36 may be constructed for example, of 60/63 Johnson Vee-wire with a 0.045 inch (0.114 cm) slot opening. Other filter designs will be evident to those skilled in the art. Alternatively, an internal reactor screen device or filter connected to the product drawoff line can be used as a means of keeping sodium from the product storage tank.

If the level control system in the reactor operates by a differential pressure measurement, it should be checked periodically to make sure that pluggage in the line is not giving a false level indication, since sodium methylate solids may gradually build up in the level dip tube. It is preferred that the dip tube be flushed out daily for about 30 seconds.

An inert atmosphere is provided in the reaction vessel. Ordinarily, the reaction vessel is flushed and maintained with an inert gas. An inert atmosphere is necessary to avoid the presence of an explosive mixture. Flushing with an inert gas (e.g., nitrogen) may be accomplished by introducing the inert gas into the reaction vessel and an inert blanket can be maintained by continuous inert gas flow.

The contents of the reaction vessel are agitated. A Chemineer Model 2HTN-3, 3 horsepower, 1750 rpm drive agitator equipped with a 29 inch carbon steel open turbine impeller may be used for such agitation.

When the continuous operation is to be ended, the flow of sodium is gradually reduced and stopped. The flow of methanol can be decreased automatically with the sodium to maintain a constant reactor temperature, or it can be reduced manually or by ratio control with the sodium. When all reactant flows have ceased, the reaction mass should be held in the reactor for about 15 minutes to complete the reaction of any sodium. If the reactor is to be shut down for an extended period of time, the reaction mass may then be discharged into storage.

The above continuous process has a number of advantages over prior art. Compared to the continuous process of German Patent No. 118,066, the need for a special solvent carrier for the sodium, the preparation of a dilute sodium dispersion in the solvent, and the solvent's removal from the product sodium methylate solution are made unnecessary. In addition, substantially higher volumetric reaction rates can be achieved.

In comparison to the batch process using sodium metal, the production capacity of a given reaction vessel for production of sodium methylate solution in continuous operation is generally more than double that of the same vessel operating in batch mode. In addition, the safety of the operation is improved by eliminating the large amount of methanol otherwise initially fed into the vessel and eliminating the temporary large excesses of sodium during each portionwise addition. The safety of the operation is also improved because sodium reacts less violently with the sodium methylate solution than with methanol itself, as it would in the initial phase of the batch reaction. Less maintenance is required for the continuous process than for the batch process because the continual startup and shutdown of the agitator, pumps and valves is eliminated.

EXAMPLE 1

An 800 gallon carbon steel reactor was equipped with a 3 horsepower agitator, feed lines for molten sodium, methanol, inert gas, reaction fluid recycle, a bottom discharge and a top vent line, generally as shown in FIG. 1. After startup as a batch process as generally described above (e.g., the reaction vessel was charged to about 60% full with a 25% solution of sodium methylate in methanol at 83° C.; and an inert atmosphere and agitation were provided). Sodium was fed at a rate of about 360 pounds (163 kg) per hour, and methanol was fed at a rate to control the temperature at 83° C., averaging about 3037 pounds (1379 kg) per hour. Reactor level was controlled at 60% full. The product was 3360 pounds/hr (1527 kg/hr) of a 25% by weight solution of sodium methylate in methanol. The yield was about 1 kg of sodium methylate (100% basis) per 0.445 kg of sodium, or 95.5% of theory.

What is claimed is:

1. A process for the continuous production of a methanol solution of sodium methylate from sodium and an excess of methanol, characterized by:

charging a reaction vessel with a solution of sodium methylate in methanol at a temperature of from about 80° to 86° C.;

providing an inert atmosphere in the reaction vessel;

agitating the contents of the reaction vessel;

adding molten sodium at a metered rate to the agitated reaction vessel;

adding methanol to the agitated reaction vessel at a rate which maintains the temperature of the reaction mass in a range of 80° to 86° C.;

reacting the sodium and methanol for a sufficient time to substantially complete the reaction of sodium; and withdrawing from the vessel a solution of sodium methylate in methanol.

2. The process of claim 1 further characterized by using a recirculation loop wherein a portion of the reaction mass is removed from the reaction vessel and transferred to a filter or screen which separates a filtered portion of the reaction mass for use as product solution and returns the remainder back to the reaction vessel.

3. The process of claim 1 further characterized by using a filter or screen placed inside the reaction vessel; wherein the product is withdrawn through the filter or screen.

4. The process of claim 1 further characterized by using a reaction pressure relief system; wherein an orifice is placed in the methanol feed line to limit the feed rate of methanol to within the design capacity of the reaction pressure relief system.

5. The process of claim 1 wherein the sodium and methanol feeds are shut off periodically for an interval sufficient to check the rate of reactor pressure decrease.

6. The process of claim 1 wherein the solution of sodium methylate in methanol is continuously withdrawn.

* * * * *